(12) United States Patent
Creswick

(10) Patent No.: US 7,488,299 B2
(45) Date of Patent: Feb. 10, 2009

(54) METHOD AND APPARATUS FOR PHYSIOLOGICAL TESTING

(75) Inventor: Richard Creswick, Strathfield (AU)

(73) Assignee: Tek Solutions Pty Ltd, Strathfield (AU)

( * ) Notice: Subject to any disclaimer, the term of this patent is extended or adjusted under 35 U.S.C. 154(b) by 0 days.

(21) Appl. No.: 11/349,532

(22) Filed: Feb. 6, 2006

(65) Prior Publication Data

US 2006/0173384 A1    Aug. 3, 2006

Related U.S. Application Data

(63) Continuation-in-part of application No. PCT/AU2004/001038, filed on Aug. 5, 2004.

(30) Foreign Application Priority Data

Aug. 7, 2003    (AU) .................... 2003904214

(51) Int. Cl.
*A61B 5/103* (2006.01)
(52) U.S. Cl. .................... 600/587; 600/595
(58) Field of Classification Search .......... 600/587
See application file for complete search history.

(56) References Cited

U.S. PATENT DOCUMENTS

| | | | |
|---|---|---|---|
| 3,501,142 A * | 3/1970 | Ingvar | .......... 482/64 |
| 4,037,480 A | 7/1977 | Wagner | |
| 4,765,613 A | 8/1988 | Voris | |
| 4,884,445 A | 12/1989 | Sadoff et al. | |
| 4,934,692 A * | 6/1990 | Owens | .......... 482/63 |
| 5,078,152 A | 1/1992 | Bond et al. | |
| 5,114,389 A * | 5/1992 | Brentham | .......... 482/53 |
| 5,158,095 A | 10/1992 | Kovacevic | |
| 5,174,154 A | 12/1992 | Edwards | |
| 5,184,628 A | 2/1993 | Shah et al. | |
| 5,348,519 A | 9/1994 | Prince et al. | |
| 5,419,562 A * | 5/1995 | Cromarty | .......... 473/269 |
| 5,722,937 A | 3/1998 | Smith | |
| 6,086,517 A * | 7/2000 | Schapmire | .......... 482/8 |

OTHER PUBLICATIONS

Lechner, et al., "Detecting Sincerity of Effort: A Summary of Methods and Approaches," (1998) *Physical Therapy* 78(8):867-888.

* cited by examiner

*Primary Examiner*—Max Hindenburg
*Assistant Examiner*—H. Q. Nguyen
(74) *Attorney, Agent, or Firm*—Carol L. Francis; Bozicevic, Field & Francis LLP

(57) ABSTRACT

A device and method to test the sincerity of physical effort of an individual. The device has a moveable member, a sensor for measuring force applied to the shaft; and a resistance means to vary the resistance to movement of the moveable member. The relationship between the varied resistive force applied to the moveable member and the measured force may be determined to establish the sincerity of effort of the user.

20 Claims, 3 Drawing Sheets

METHOD AND APPARATUS FOR PHYSIOLOGICAL TESTING

CROSS-REFERENCE TO RELATED APPLICATIONS

This is a continuation in part of International patent application No PCT/AU2004/001038 published as WO 2005/013821, the entire contents of which are incorporated herein by reference.

FIELD OF THE INVENTION

This invention relates to a method and apparatus for measuring the performance of human joints.

BACKGROUND OF THE INVENTION

The present invention is concerned with measuring the performance of a joint or combination of such in the human body and, in particular, to measuring the effort exerted by a patient during the performance testing process.

When persons suffer injuries in accidents such as those which commonly occur in the workplace, and in road traffic accidents, it is usually necessary for the extent of the injured person's injuries to be determined in order to assess the correct amount of compensation which may be payable to the injured person as a result of the accident. Typically the compensation payable will be related to the extent of the person's injuries and the loss of use or performance of parts of the person's body due to the accident. For example, if a person injures their arm in an accident the compensation payable will depend on the extent to which that person's use of their arm has been impaired. Further, an accurate assessment of an injury allows a rehabilitation programme to be monitored and varied if necessary.

However, there is currently no satisfactory repeatable scientific method of assessing a person's joint performance to determine to what extent the performance of the joint has been impaired due to injury or accident or the like. Currently, most injuries are assessed subjectively by doctors or physiotherapists. The assessment process is generally unscientific and open to inaccuracies. One particular problem occurs when patients pretend to be more seriously injured than they are for example by pretending to be unable to do particular tasks or by only providing a sub-maximal effort when tested.

This is a major problem for organisations which provide insurance payments related to injuries, particularly insurance companies.

A further related problem arises, in that since it is not possible to accurately measure joint performance, it is not possible to accurately measure improvement in joint performance. Thus if a patient is undergoing physiotherapy or other treatment for injuries associated with a joint it is not, for example, possible to accurately plot improvement or lack of fit in the joint on a week by week basis.

The present invention aims to provide a device for repeatedly and accurately measuring the performance of a joint in the body and which preferably includes means for determining whether the patient whose joint performance is being measured is making a minimal or at least sub-maximal effort, when tested.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

In one aspect, the present invention provides a device for performance testing of a human's joints comprising:
 a moveable member;
 a sensor for measuring force applied to the moveable member by the human; and
 a resistance means for varying the resistance to movement of the moveable member at least once during a single movement of the moveable member by the human; and
 means for comparing, or determining the correlation between, the measured force applied to the movable member with the resistance to movement of the movable member for assessing the response of the human to the variation in resistance to provide an indication of the human's sincerity of effort in moving the movable member.

The moveable member may be a shaft or a lever.

Alternatively, the movable member may be a piston in a hydraulic cylinder.

Many other types of movable member may be possible, such a brakes sliding on a bar or shaft.

Mechanisms, such as chains or belt and sprocket drives, may be connected to the movable member to convert rotational or linear movement of the member to other types of movement. For example, a cable/capstan and angle sensing device could be used for handling linear/compound movement.

Where the moveable member is a shaft, the shaft may be rotatable. In this embodiment, the sensor may comprise a torque sensor for measuring torque applied to the shaft.

Where the movable member is a piston of a hydraulic cylinder, the sensor may comprise a pressure sensor measuring the fluid pressure inside the cylinder. An adjustable control valve, controlling the exit of fluid from the cylinder.

Two or more cylinders acting together could be used.

The resistance means may comprise a coupling means that variably couples the shaft to the torque sensor. Such variable coupling of shaft and torque sensor varies the resistance to the turning of the shaft. An example of such a resistance means is an electric brake, eddy coupling, servo motor or the like.

Where the resistance means comprises a coupling means, typically the resistance is variable between a state where there is no coupling and no resistance is applied and the shaft is free to rotate relative to the torque sensor and a state in which the shaft is fully coupled to the torque sensor.

It is preferred that the device includes an encoder for measuring the position of the shaft. The device may also include a control means for receiving input data from the torque sensor. The control means may also be arranged to input control signals to the resistance means and to determine the relationship between the resistance applied to the shaft and the torque measured by the torque sensor. Further, the control means may receive signals from the encoder in relation to the angular position of the shaft.

Where the moveable member comprises a lever, said lever may be connected to a resistance means. The resistance means may comprise a pump member. The pump member typically has a control valve to vary resistance to the lever. Further, the pump member of this embodiment may be connected to a sensor, said sensor measuring the force applied to the lever. The sensor may comprise a pressure gauge to measure the pressure change of fluid in the pump as force is applied to the lever.

A number of devices may be operated together simultaneously to deal with movement in multiple axes.

In one broad related aspect, the present invention provides a method of sincerity of effort testing of a person's joint performance by repeatedly measuring the response of that joint to a varying load.

More specifically, the present invention provides a method of measuring a person's joint performance and simultaneously measuring sincerity of effort by getting the person to apply force to a movable member to move that member;

varying the resistance to movement of the member at least once during a single movement;

measuring the force applied to the member by the person, recording the resistive force applied; and assessing the correlation between the resistive force applied and the measured torque to thereby assess the sincerity of effort applied by the person to movement of the member.

In a related aspect, the invention provides a method of sincerity of effort testing of a person's joint performance by measuring the torque applied to a shaft by one of the person's joints comprising the steps of:

applying a varying resistive force to turning of the shaft, the resistance to turning of the shaft being varied at least once during a single movement;

measuring the torque applied to the shaft;

recording the resistive force applied; and assessing the correlation between the resistive force applied and the measured torque to provide an indication of the sincerity of effort applied by the person to movement of the shaft.

BRIEF DESCRIPTION OF THE DRAWINGS

A specific example of the present invention will now be described by way of example only and with reference to the accompanying drawings in which.

DETAILED DESCRIPTION OF A PREFERRED EMBODIMENT

Figure 1:
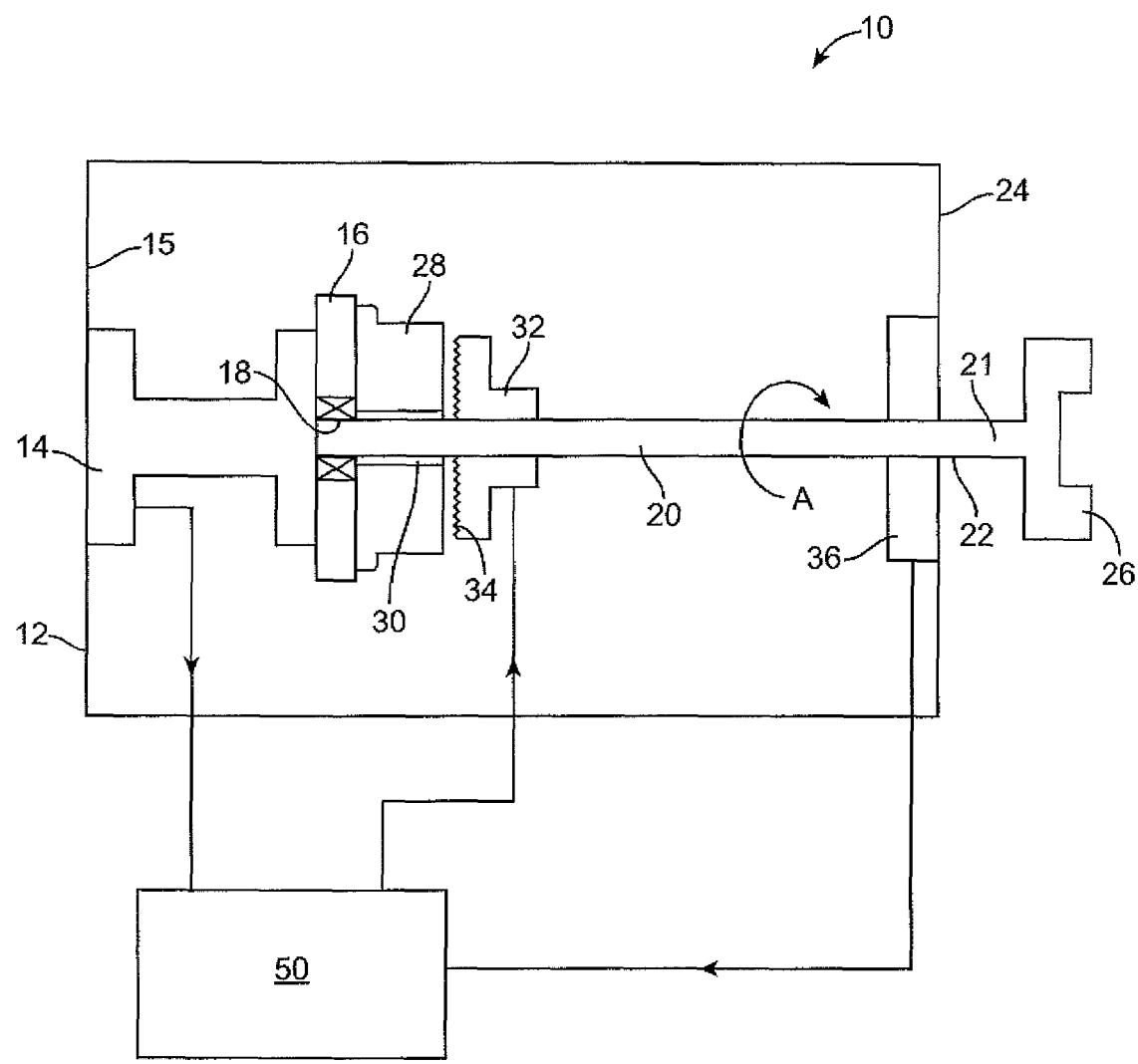
FIG. 1 is a schematic drawing of a device for repeated performance measuring to gauge sincerity of effort.

Referring to the drawings, in particular FIG. 1, the device generally indicated at 10, includes a rectangular box-like casing 12. One side of a torque sensor 14 is mounted to one interior wall 15 of the casing. Fixed to the opposite side of the torque sensor 14 is a mounting plate 16 defining a central hole 18 through which one end of an elongate shaft 20 extends. The end of the shaft 20 is free to rotate relative to the mounting plate and the torque sensor 14. The shaft 20 extends from the mounting plate 16 co-axial with the torque sensor 14 and defines a free end 21 which projects through an aperture 22 defined in a wall 24 of the casing opposite to the wall 15 to which the torque sensor 14 is mounted.

The free end 21 of the shaft 20 defines a coupling 26 which can be attached to various joint testing interfaces for testing any joints or combinations of such which can be used to produce rotary motion about an axis, which most if not all joints are capable of.

A brake stator coil 28 defining a central bore 30 which is of greater diameter than the shaft is fixed to the mounting plate 16. The shaft 20 extends through that central bore 30. A brake rotor 32 is mounted on the shaft 20 and defines a friction surface 34 facing the brake stator coil 28 and in conjunction with the brake stator coil 28 defines an electric brake. Increasing the current supplied to the brake rotor 32 increases the resistance between the brake rotor 32 and the brake stator coil 28 and hence the coupling between the two. When the current is a maximum and the brake is fully on any torque applied to the shaft 20 is transmitted directly to the torque sensor 14. When the brake is fully disengaged, the shaft 20 spins freely and no torque is applied to torque sensor 14. A shaft encoder 36 mounted on the wall 24 of the casing measures the angular position of the shaft 20.

A computer control means in the form of a micro controller 50 is connected to the torque sensor 14 and the shaft encoder 36 and receives input signals indicative of the torque measured by the torque sensor and the angular position of the shaft as measured by the shaft encoder. The micro controller also controls the current applied to the electric brake via a feedback loop.

When a torque is applied to the shaft 20 to turn the shaft in the direction A, that torque is measured by the torque sensor 14.

It will be appreciated that the device 10 works by using the brake rotor 32 and brake stator coil 28 to provide increasing resistance to the turning of the shaft 20 about its longitudinal axis which is measured by the torque sensor 14. The resistance can be quickly and accurately controlled by varying the current applied to the brake rotor 32. The torque applied to the shaft 20 is measured by the torque sensor 14 and this therefore gives a measurement of the performance of a patient's joint or combination.

The performance of virtually any joint can be measured using a flexible rope and a capstan fitted to coupling 26 to monitor movement of the joint. It will be readily appreciated that other mechanisms may be fitted to the coupling to convert rotational movement to other types of movement for testing other types of movement. It is also envisaged that two or three devices could be operated simultaneously in different axes at the same time to test the performance of more complex actions in three dimensions such as serving a tennis ball, kicking a football or the like.

However, simply measuring the performance of the joint as described above, by measuring the torque a joint may generate will not measure true joint performance unless a patient is trying as hard as they can i.e. giving maximal effort. Also simply measuring performance based on application of a fixed load does not provide an indication of the sincerity of effort that a patient is applying to the task.

Thus, in order to make it more difficult to misrepresent the true performance test by making a sub-maximal effort, in a particularly preferred embodiment, the computer control means 50 is programmed to vary the resistive load provided by the electric brake, whilst the shaft 20 is being turned by the patient. This makes it much more difficult for a patient to misrepresent the test since whilst it is relatively straightforward to decide to make a "50% effort, say, when moving against an unchanging resistance, when the resistance changes continuously, the patient is unable to accurately and quickly calculate the changing level of effort they need to apply to be consistent with their original level of effort.

The system thus varies the resistive load applied to the electric brake, changing the resistance to turning of the shaft by the patient. The device 10 measures the torque applied to the shaft 20 by the patient and correlates the measured torque with the resistance applied to the turning of the shaft 20.

The device 10 rapidly varies the resistance to the turning of the shaft 20 during a single exercise performed by the patient. Thus, if the patient is asked to, say, pull his/her fist up to his shoulder, in that one movement, the resistance to the turning of the shaft would vary several times.

Several patterns of resistance may be applied including sinusoidal, "saw tooth" and non-uniform patterns. The patterns depicted in FIGS. 2 and 3 are of a step change nature.

Figure 2:
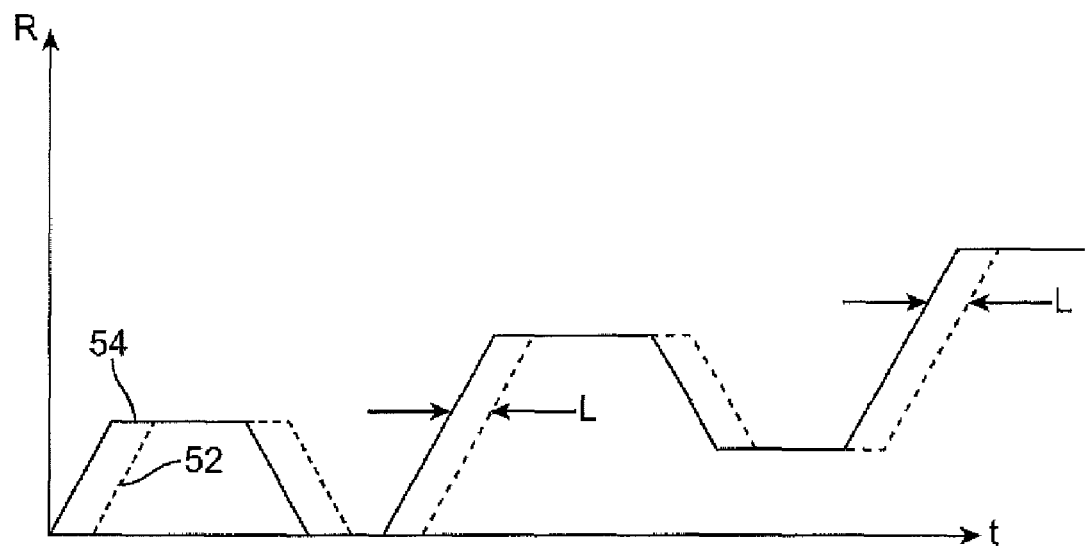
FIGS. 2 and 3 are graphs comparing the resistive load applied to the device against measured torque.
Figure 3:
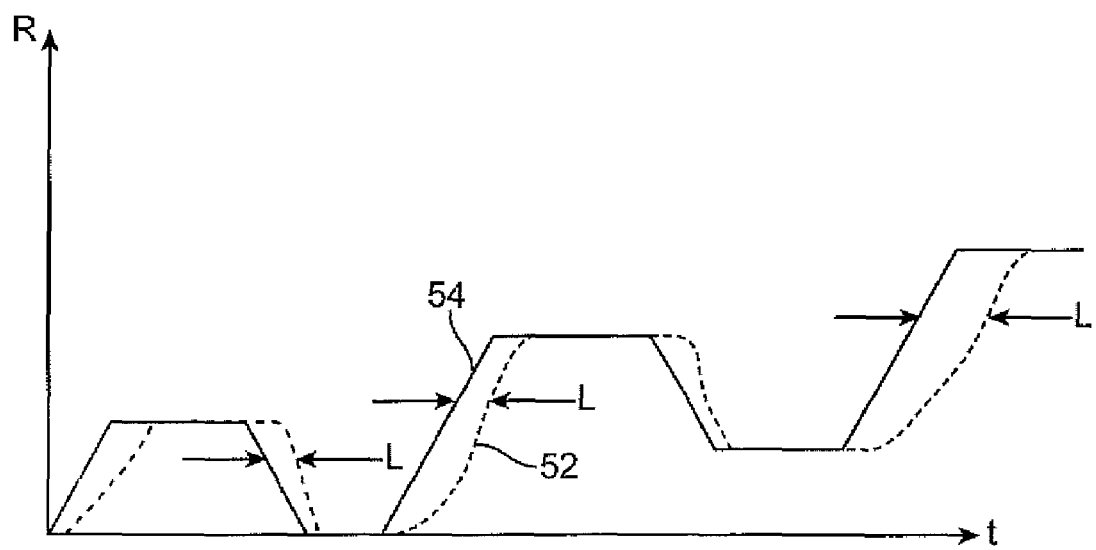

With reference to FIG. 2 for a patient who is making a 100% effort each time, the relationship L between the measured torque 52 and the resistance applied 54 is shown to be fairly constant. If however, a patient is attempting to cheat the test by making only a "50% effort", then they will not be able to maintain that sub-maximal 50% effort consistently as the load is varied and a greater variation/standard deviation in the relationship L of the measured torque and the resistive force will be measured, as shown in FIG. 3. The tests may also be repeated, with variations in the patient's performance further indicating sub-maximal effort.

The variation of the resistive load may be based on position of the shaft as measured by either the encoder or time. The variation may be continuously varied for example by a ramped load or a stepped load or both. The variation may be increasing or decreasing or consistent stopping.

The electric brake may be replaced by an equivalent element such as an eddy current coupling or similar controlled coupling device or servomotor. Further, the method of providing a variable resistance could be a hydraulic motor or actuator with a variable flow control so that the oil flow could be restricted to provide a controlled resistive torque.

The system may be active or passive. For example, in an active system, the resistive electric brake could be replaced by a variable torque servo drive.

Because the device provides a repeatable way of measuring joint performance, it is possible to measure improvement in joint performance, for example, the performance of an elbow could be measured on a weekly basis and increases in the strength and range of movement of the joint performance measured and tracked.

It will appreciated by those skilled in the art that many of various well known algorithms and statistical techniques can be used for providing figures correlating the patient's effort to the load or resistance. The particular algorithm used is not critical.

Coefficient of Correlation—Mathematical and or Visual methods

One suitable formula is:

$$r = \frac{\Sigma XY - \frac{\Sigma X \Sigma Y}{N}}{\sqrt{\left(\Sigma X^2 - \frac{(\Sigma X)^2}{N}\right)\left(\Sigma Y^2 - \frac{(\Sigma Y)^2}{N}\right)}}$$

Using this algorithm, the correlation coefficient is used to determine the relationship between two properties, Y and X being values of the force applied by the patient and the applied resistance, respectively.

Another form is:

$$\text{Correlation Coefficient} = \frac{Cov(X, Y)}{(StdDevX)(StdDevY)}$$

Where:

$-1 <= \text{Correlation Coefficient} <= 1$

And:

$Cov(X, Y) = 1/n\Sigma(x^i - x)(y^i - y)$ where y and x are the values of the force applied by the patient and the applied resistance, respectively.

A correlation coefficient of +1.0 is a strong positive result. As x goes up, y always goes up. A correlation of +0.5 is a weak positive, with y tending to go up as x does. A correlation coefficient of 0 shows no correlation, with 0.5 being weak negative and −1.0 being a strong negative.

A positive number close to 1 indicates a high degree of correlation and strongly suggests sincerity of effort.

Figure 4:
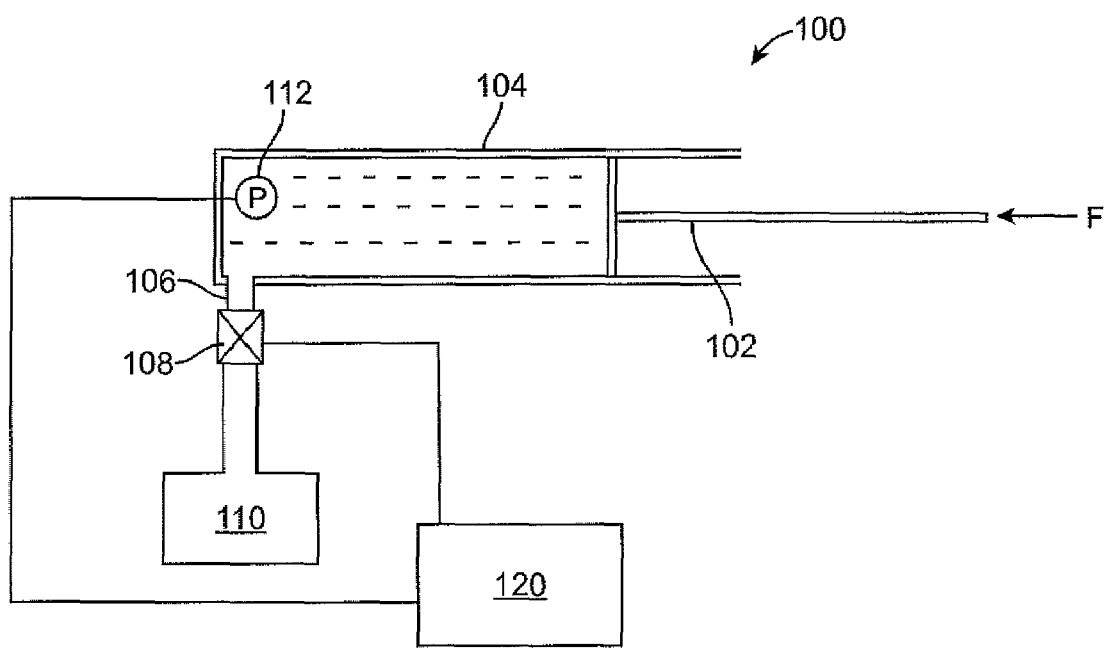
FIG. 4 is a schematic drawing of a second embodiment of a device for testing sincerity of effort.

FIG. 4 illustrates a further embodiment of a device for performance testing of joints. The movable member in this embodiment is a piston 102 slideable within a cylinder 104 containing hydraulic fluid. Forces F acting to push the piston into the cylinder cause the pressure in the hydraulic cylinder to increase and the discharge of hydraulic fluid through an exit pipe 106. An electrically operable adjustable control valve 108 controls the ease of flow through the exit pipe by varying its degree of closure. Expelled hydraulic fluid may pass into a reservoir 110. A pressure sensor 112 in the hydraulic cylinder measures the pressure therein which depends on the force F applied to the piston. The sensors measurements are sent to a computer control means 120 which also controls the valve 108. The degree of resistance to movement of the piston may be varied by the control valve 108. By comparing that with the measure pressure the correlation between the force applied and the resistance to movement can be calculated by a computer control means 120 which controls the degree of opening of the valve and receives and input from the pressure sensor 112 measuring the hydraulic pressure in the cylinder. By varying the resistance to movement of the piston as a patient pushes the piston into the cylinder, the relationship between the applied force and resistance can be measured, to test the patient's sincerity of effort by determining the variation between the two.

It will be appreciated by persons skilled in the art that numerous variations and/or modifications may be made to the invention as shown in the specific embodiments without departing from the spirit or scope of the invention as broadly described.

The present embodiments are, therefore, to be considered in all respects as illustrative and not restrictive.

The invention claimed is:

1. A method of measuring a person's joint performance and simultaneously measuring sincerity of effort comprising:
    providing a movable member to be moved by a single movement of one or more joints of the person;
    rapidly varying the resistance to movement of the member at least once during the single movement;
    measuring the force applied to the moveable member by the person during at least the single movement,
    recording the resistance applied to the movable member;

inputting the resistance applied and the measured force applied into a means for calculating the correlation between the measured force applied to the movable member during the single movement and the resistance to movement of the movable member; and outputting a coefficient of correlation indicative of the correlation between the measured force applied to the movable member during the single movement and the resistance to movement of the movable member, wherein the coefficient of correlation provides an indication of the human's sincerity of effort in moving the movable member.

2. A method of sincerity of effort testing of a person's joint performance by measuring the torque applied to a shaft by one of the person's joints comprising:

applying a varying resistance to turning of the shaft, the resistance to turning of the shaft being rapidly varied at least once during a single movement;

measuring the torque applied to the shaft by the person during at least the single-movement;

recording the resistance applied to the shaft; and inputting the resistance applied and the measured torque applied into a means for calculating the correlation between the measured torque applied to the shaft during the single movement and the resistance to movement of the shaft; and outputting a coefficient of correlation indicative of the correlation between the measured torque applied to the shaft during the single movement and the resistance to movement of the shaft, wherein the coefficient of correlation provides an indication of the human's sincerity of effort in moving the shaft.

3. A method of measuring a person's joint performance and simultaneously measuring level of effort comprising:

providing a movable member having a variable resistance to movement, wherein the person applies a force to the moveable member to move the moveable member;

rapidly varying the resistance to movement of the moveable member at least once during a single movement;

measuring the force applied to the moveable member by the person during at least the single movement, recording the resistance applied to the moveable member; and inputting the resistance applied and the measured force applied into a means arranged to display a graph of the measured force applied to the movable member during the single movement superposed over the resistance to movement of the movable member corresponding to movement of the moveable member by the person; and displaying a comparative graph of the measured force applied to the movable member during the single movement superposed over the resistance to movement of the movable member, thus providing a visible indication of the human's sincerity of effort in moving the movable member.

4. A method as claimed in any one of claims 1, 2 or 3 wherein the method is carried out over a single movement of the person's joint.

5. A method of measuring a person's joint performance and simultaneously measuring sincerity of effort comprising:

providing a movable member to be moved by a single movement of one or more joints of the person;

measuring the force applied to the movable member by the person during at least the single movement in which a resistance to movement of the moveable member is rapidly varied at least once during the single movement;

recording the resistance applied to movement of the moveable member;

inputting the resistance applied and the measured force applied into a computer control means; and displaying a comparative graph of the measured force applied to the movable member when the resistance is varied during the single movement superposed over the resistance applied to movement of the movable member, thus providing a visible indication of the human's sincerity of effort in moving the movable member when the resistance is varied.

6. A method of measuring a person's joint performance and simultaneously measuring sincerity of effort comprising:

providing a movable member to be moved by a joint movement of the person;

measuring the force applied to the movable member by the person during the joint movement in which a resistance to movement of the moveable member is rapidly varied at least once during a single movement of the joint;

recording the resistance applied to the moveable member;

inputting the resistance applied and the measured force applied into a means for calculating the variation or standard deviation of the relationship between the measured force applied to the movable member and the resistance to movement of the movable member; and displaying the variation or standard deviation of the relationship between the measured force applied to the movable member when the resistance is varied during the single movement and the resistance to movement of the movable member, wherein the variation of standard deviation provides an indication of the human's sincerity of effort in moving the movable member when the resistance is varied.

7. A performance testing device for performance testing of a human's joints and assessing the response of the human to a rapid variation in resistance comprising:

a moveable member, wherein the movable member may be moved about an axis against a resistance by action of one or more of the human's joints during a single movement of said one or more joints;

a sensor for measuring a force applied to the moveable member by the human, wherein the sensor transmits a first signal indicative of the measured force applied to the movable member to a control means;

a resistance means for applying the resistance to movement of the same moveable member from which the sensor is measuring the force applied; and the control means, arranged to rapidly vary the resistance applied to the movable member at least once during the single-movement, and wherein the control means records a second signal indicative of the resistance applied to the movable member, wherein the control means is arranged to calculate the variation or standard deviation of the relationship between the measured force applied to the movable member when the resistance is varied and the resistance to movement of the movable member, wherein the variation or standard deviation is indicative of the correlation between the measured force applied to the movable member when the resistance is varied and the resistance to movement of the movable member, thus providing an indication of the human's sincerity of effort in moving the movable member when the resistance is varied.

8. The device of claim 7 wherein the moveable member comprises a shaft.

9. The device of claim 8 wherein the sensor comprises a torque sensor for measuring torque applied to the shaft.

10. The device of claim 9 comprising a coupling means variably coupling the shaft to the torque sensor and under control of the control means thereby varying the resistance to turning of the shaft.

11. The device of claim 10 wherein the coupling is continuously variable between a state where there is no coupling between the shaft and the torque sensor and a state in which the shaft is fully coupled to the torque sensor.

12. The device of claim 10 wherein the coupling means comprises an electric brake.

13. The device of claim 9 wherein the control means receives input data from the torque sensor, said input data indicative of the torque applied to the shaft by the human.

14. The device of claim 13 further comprising an encoder for measuring the position of the shaft.

15. The device of claim 14 wherein the control means also receives signals indicative of the angular position of the shaft from the encoder.

16. The device of claim 7 wherein the control means is arranged to vary the resistance more than once during the single movement.

17. The device of claim 7 wherein the control means is arranged to vary the resistance once during the single movement.

18. The device of claim wherein the control means is arranged to vary the resistance in a step change fashion.

19. The device of claim 7 wherein the resistance means comprises an electric brake.

20. The device of claim 7 wherein the resistance means comprises a valve.

* * * * *